US00PP13487P3

(12) United States Plant Patent
Olesen et al.

(10) Patent No.: US PP13,487 P3
(45) Date of Patent: Jan. 21, 2003

(54) MINIATURE ROSE PLANT NAMED 'POULRA001'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 25 days.

(21) Appl. No.: 09/774,257

(22) Filed: Jan. 29, 2001

(65) Prior Publication Data

US 2002/0152512 P1 Oct. 17, 2002

(51) Int. Cl.[7] ..... A01H 5/00

(52) U.S. Cl. ..... Plt./121

(58) Field of Search ..... Plt./121, 122, 118, Plt./117, 116, 119

*Primary Examiner*—Bruce R. Campell
*Assistant Examiner*—Annette Para

(57) ABSTRACT

A new miniature rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

Botanical: *Rosa hybrida* 'POULra001'.

Commercial: Miniature.

The present invention constitutes a new and distinct variety of miniature rose plant which originated from a controlled crossing between an unnamed and unpatented seedling and 'POULhilda', described and illustrated in U.S. Plant patent application Ser. No. 09/607,330 dated Jun. 30, 2000. The two parents were crossed and the resulting seeds were planted in a controlled environment. The new variety is named 'POULra001'.

The new rose may be distinguished from its seed parent, an unnamed seedling, by the following combination of characteristics:

1. The seed parent's blooms are orange-red whereas 'POULra001' has pink blooms.

2. The seed parent's habit is taller than the applicant variety.

The new variety may be distinguished from its pollen parent, 'POULhilda' created by the same inventors, by the following combination of characteristics:

1. The pollen parent has lighter pink blooms compared to 'POULra001'.

2. 'POULac001' is more compact than the pollen parent.

The objective of the hybridization of this rose variety for commercial culture was to create a new and distinct variety with unique qualities, such as:

1. Uniform and abundant pink flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

This combination of qualities is not present in previously available commercial cultivars of this type and distinguish 'POULra001' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark. 'POULra001' was selected by the inventors as a single plant from the progeny of the hybridization in the spring of 1998.

Asexual reproduction of 'POULra001' by cuttings and traditional budding was first done by L. Pernille and Mogens N. Olesen in their nursery in Fredensborg, Denmark in June 1998. This initial and other subsequent propagations conducted in controlled environments have demonstrated that the characteristics of 'POULra001' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra001'. Specifically illustrated in SHEET 1:

1. Stem showing the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULra001', as observed in its growth in greenhouse environment in Burlington, Ontario, Canada, on plants aged 15 weeks. Color references are made using The Royal Horticultural Society (London, England) Colour Chart, 1995, except where common terms of color are used.

For a comparison, several physical characteristics of the rose variety 'POULcar', a rose variety from the same inventors described and illustrated in U.S. Plant Pat. No. 7,999 and issued on Oct. 13, 1992 are compared to 'POULra001' in Chart 1.

CHART 1

| | 'POULra001' | 'POULcar' |
|---|---|---|
| Open bloom size | 40–50 mm | 25–30 mm |
| Color of bud upon opening | Red Group 39B | Red Group 38C |
| Petalage | Very double 50–60 petals | Very double 60 petals |

Parents: Unnamed seedling×'POULhilda'.
Classification:
*Botanical.*—*Rosa hybrida.*
*Commercial.*—Miniature.

FLOWER AND FLOWER BUD

Blooming habit: Continuous.
Flower bud:
*Size.*—Upon opening, 18–22 mm in length from base of receptacle to end of bud.
*Bud form.*—Short, pointed-ovoid.
*Bud color.*—As sepals unfold, Red Group 39B. Red Group 52C at ¼ opening.
*Sepals.*—Green Group 143A. Weak foliaceous appendages on three of the five sepals. Surfaces of sepals strongly pubescent. Stipitate glands are present on margins of sepals and the foliaceous appendages. Sepals are 30 mm long and 12 mm wide.
*Receptacle.*—Surface: Smooth. Shape: Urn-shaped. Size: Small. 5 mm (h)×6 mm (w). Color: Green Group 143B.
*Peduncle.*—Surface: Smooth. Length: 35 to 50 mm average length. Color: Yellow-Green Group 144A. Strength: Strong.
*Borne.*—Multiple (1–3) buds per stem.
*Anthocyanin.*—None.
Flower bloom:
*Fragrance.*—None.
*Duration.*—As a pot plant, flowers last from 15 to 20 days. As a cut flower 6 to 8 days. Petals fall cleanly from the plant.
*Size.*—Large for an 8–11 cm pot rose. Average flower diameter is 40–50 mm when open.
*Form.*—Flowers when fully open are partially quartered. Shape of flower when viewed from the side: Upon opening, upper part: Flat. Upon opening, lower part: Flat. Open flower, upper part: Flat. Open flower, lower part: Flattened convex.
*Petalage.*—Very double. Average range: 50–60 petals under normal conditions with 0–5 petaloids.
Color:
*Upon opening, petals.*—Outermost petals: Outer Side: Red Group 52D. Inner Side: Red Group 48C. Innermost petals: Outer Side: Red Group 48C. Inner Side: Red Group 48C.
*Upon opening, basal petal spots.*—Outermost petals: Outer Side: Green Group 143D. Inner Side: Yellow-Green Group 144D. Innermost petals: Outer Side: Yellow-Green Group 149C. Inner Side: Yellow-Green Group 150C.
*After opening, petals.*—Outermost petals: Outer Side: Red Group 54D. Inner Side: Red Group 55C. Innermost petals: Outer Side: Red Group 55D. Inner Side: Red Group 55C.
*After opening, basal petal spots.*—Outermost petals: Outer Side: Green-Yellow Group 1D. Inner Side: Yellow Group 3B. Innermost petals: Outer Side: Yellow Group 3A. Inner Side: Yellow Group 3A–B, with intonations of Yellow Group 3A–B emanating from basal petal spot well into middle zone of the petal.
General tonality: On open flower Red Group 50D. No change in the general tonality at the end of the 5th day. Afterwards, general tonality is Red Group 49C.
Petals:
*Petal reflex.*—Slightly.
*Petal edge.*—Uniform with slight point in center margin.
*Shape.*—Deltoid. Apex is mucronate. Margin is entire.
*Petaloids.*—Quantity: 0–5. Texture: Smooth. Color: Red Group 50D.
*Thickness.*—Thin.
*Arrangement.*—Imbricated.
*Texture.*—Smooth.
Reproductive organs:
*Pollen.*—Color: Greyed-Orange Group 173A. Quantity: Average.
*Anthers.*—Size: 2 mm long. Color: Greyed-Yellow 160C. Quantity: 25 to 30.
*Filaments.*—Color: Yellow Group 9B. Length: 8 mm.
*Stigmas.*—Are superior in location to the anthers (1–2 mm taller). Color: Yellow-Green Group 150B. Length: 9 mm.
*Styles.*—Color: Yellow-Green Group 150D. Quantity: 30 to 40.
*Seed formation.*—None in pot plants.

PLANT

Plant growth: Vigorous and compact. When grown as an 8–11 cm pot plant, the average height of the plant is 16–20 cm and the average width is 14–18 cm.
Stems:
*Color.*—Young wood: Yellow-Green Group 144A. Older wood: Yellow-Green Group 144A.
*Prickles.*—Incidence: Few. Size: Average length: 2–4 mm. Color: Yellow-Green Group 143B with intonations of Greyed-Red 180D at tips of prickles. Shape: Linear to slightly concave.
*Surface.*—Young wood: Smooth. Older wood: Smooth.
Plant foliage: Normal number of leaflets on normal leaves in middle of the stem: 5 leaflets.
*Leaf size.*—Small. 65–70 mm (l)×40–50 mm (w).
*Abundance.*—Average.
*Color.*—Mature Foliage: Upper Leaf Surface: Yellow-Green Group 147A. Lower Leaf Surface: Yellow-Green Group 146B. Juvenile foliage: Upper Leaf Surface: Yellow-Green Group 144A. Lower Leaf Surface: Yellow-Green Group 144B. Anthocyanin: Intonations of Red-Purple Group 60A on juvenile leaf margins.
Plant leaves and leaflets:
*Stipules.*—Size: 4–5 mm (l), 3–4 mm (w). Color: Yellow-Green Group 147B. Stipitate glands: Present along margins. Anthocyanin: None.
*Petiole.*—Length: 20–25 mm. Color: Yellow-Green Group 146B. Underneath: Smooth. Margins: Stipitate glands along margins. Anthocyanin: On juvenile foliage, upper surface. Color: Greyed-Purple Group 183B.

*Rachis.*—Color: Yellow-Green Group 146C. Underneath: Smooth with small prickles where leaflet attaches. Margins: Stipitate glands present on upper surface. Anthocyanin: Upper surface of juvenile and mature foliage. Color: Greyed-Purple Group 183B.

*Leaflet.*—Edge: Serrated. Shape: Ovate. Other: Moderately glossy and thin.

Disease resistance: Above average resistance to mildew, black spot, and Botrytis under normal growing conditions in Jackson County, Oreg.

Cold hardiness: The variety 'POULra001' has been found to be resistant to damage from cold in USDA Zone 7.

We claim:

1. A new and distinct variety of rose plant of the miniature class, substantially as herein illustrated and described as a distinct and novel rose variety due to its abundant, pink flowers, vigorous growth, compact habit, suitability for production from softwood cuttings in pots, and durable flowers and foliage which make the variety suitable for distribution in the floral industry.

* * * * *

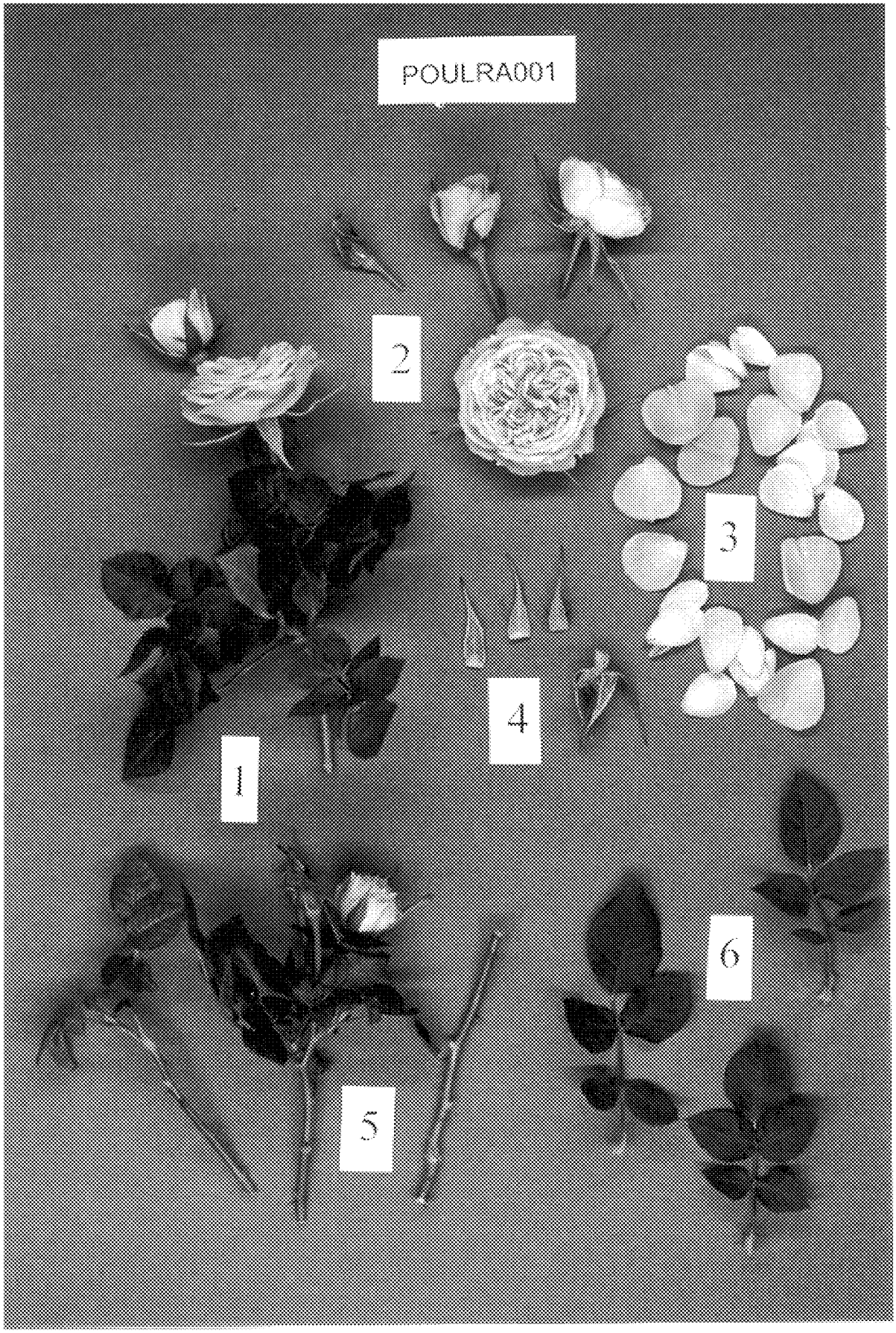
POULRA001
2
3
4
1
6
5